United States Patent
Beekman et al.

(10) Patent No.: US 7,598,406 B2
(45) Date of Patent: Oct. 6, 2009

(54) PRODUCTION OF ETHYLENE OXIDE

(75) Inventors: Willem Johan Beekman, Delft (NL);
Peter Boons, Amsterdam (NL);
Wiebren Age Miedema, Moerdijk (NL);
Dominicus Maria Rekers, Amsterdam (NL)

(73) Assignee: Shell Oil Company, Houston, TX (US)

( * ) Notice: Subject to any disclaimer, the term of this patent is extended or adjusted under 35 U.S.C. 154(b) by 619 days.

(21) Appl. No.: 11/382,624

(22) Filed: May 10, 2006

(65) Prior Publication Data

US 2006/0264648 A1 Nov. 23, 2006

(30) Foreign Application Priority Data

May 10, 2005 (EP) .................... 05252851

(51) Int. Cl.
*C07D 301/32* (2006.01)
(52) U.S. Cl. .................... 549/541; 549/542; 549/538
(58) Field of Classification Search ................ 549/541, 549/542, 538
See application file for complete search history.

(56) References Cited

U.S. PATENT DOCUMENTS

| | | | | |
|---|---|---|---|---|
| 2,156,341 A | 5/1939 | Langwell et al. | ............ | 260/348 |
| 2,771,473 A | 11/1956 | Courter | ............ | 260/348 |
| 3,097,215 A | 7/1963 | Courter et al. | ............ | 260/348 |
| 3,140,153 A | 7/1964 | Huckins, Jr. | ............ | 23/220 |
| 3,165,539 A | 1/1965 | Lutz | ............ | 260/348 |
| 3,174,262 A | 3/1965 | Lutz | ............ | 55/48 |
| 3,217,466 A | 11/1965 | Bogart | ............ | 55/44 |
| 3,418,338 A | 12/1968 | Gilman et al. | ............ | 260/348 |
| 3,729,899 A | 5/1973 | Cunningham et al. | ............ | 55/44 |
| 3,745,092 A | 7/1973 | Venderwater | ............ | 203/42 |
| 3,766,714 A | 10/1973 | Cunningham et al. | ............ | 55/48 |
| 3,856,484 A | 12/1974 | Cocuzza et al. | ............ | 55/48 |
| 3,964,980 A | 6/1976 | Ozero | ............ | 203/42 |
| 4,028,070 A | 6/1977 | Uchii et al. | ............ | 55/48 |
| 4,033,617 A | 7/1977 | Cocuzza et al. | ............ | 203/27 |
| 4,134,797 A | 1/1979 | Ozero | ............ | 203/75 |
| 4,469,492 A | 9/1984 | Lagana et al. | ............ | 55/49 |
| 4,508,927 A | 4/1985 | Bhise et al. | ............ | 568/858 |
| 4,529,417 A | 7/1985 | Lagana et al. | ............ | 55/84 |
| 4,555,251 A | 11/1985 | Jonsson et al. | ............ | 55/48 |
| 4,597,833 A | 7/1986 | Neel et al. | ............ | 203/49 |
| 4,778,567 A | 10/1988 | Kakimoto et al. | ............ | 203/23 |
| 4,875,909 A | 10/1989 | Kakimoto et al. | ............ | 55/40 |
| 4,966,657 A | 10/1990 | Delannoy et al. | ............ | 203/76 |
| 5,529,667 A | 6/1996 | Coffey | ............ | 203/96 |
| 6,551,465 B1 | 4/2003 | Van Zile et al. | ............ | 202/158 |
| 6,833,057 B1 | 12/2004 | Bessling et al. | ............ | 203/14 |

FOREIGN PATENT DOCUMENTS

EP 0870753 10/1998

OTHER PUBLICATIONS

Kirk-Othmer Encyclopedia of Chemical Technology, $3^{rd}$ edition, vol. 9, 1980, pp. 443 to 447.

*Primary Examiner*—Elvis O Price (57) ABSTRACT

Process for the recovery of ethylene oxide (EO) from fat absorbent (FA) which comprises providing a feed of elevated temperature FA to an EO Stripper, providing a stripping gas feed and contacting the stripping gas feed at elevated temperature with the elevated temperature FA feed, obtaining stripped lean absorbent (LA) and an EO-containing gas, and providing one or more external process stream feeds to the EO Stripper at a location above the elevated temperature FA feed and at a lower temperature with respect to the elevated temperature FA feed thereby concentrating EO in the EO-containing gas. The process can also include one or more impurity removal stages in the form of one or more side draws from the EO Stripper or an EO Stripper Concentrator. The invention also includes an apparatus for performing the process.

12 Claims, 6 Drawing Sheets

Fig.1.

Prior Art

PRODUCTION OF ETHYLENE OXIDE

CROSS-REFERENCE TO RELATED APPLICATIONS

This application claims the benefit of European Patent Application No. 05252851.0, filed May 10, 2005 which is incorporated herein by reference.

FIELD OF THE INVENTION

The present invention relates to the production of ethylene oxide, most suitably within an integrated ethylene oxide/ethylene glycols process.

BACKGROUND OF THE INVENTION

Ethylene oxide (EO) is an intermediate product for making a wide variety of derivatives, the most important derivatives in terms of volume being the ethylene glycols (EG). Other derivatives include ethanolamines, glycol ethers, detergent ethoxylates, polyols and others. EG is produced by the reaction of EO with water, producing mono ethylene glycol (MEG) as the main product with di ethylene glycol (DEG) and tri ethylene glycol (TEG) as by-products.

MEG is mainly used for the manufacture of polyester fibres, polyethylene terephthalate (PET) and, to a lesser extent, in the cooling systems of motor vehicles where it serves as antifreeze. DEG is also used in the fibre industry and as tobacco humectant. DEG and TEG are both used for gas drying. TEG is also used in the manufacture of cellophane for food packaging.

The production of ethylene oxide is described in Kirk-Othmer Encyclopedia of Chemical Technology, $3^{rd}$ edition, Volume 9, 1980, pages 443 to 447. The production of ethylene glycols is described in Ullmann's Encyclopedia of Industrial Chemistry, $5^{th}$ edition, Volume A 10, 1987, pages 104 and 105.

EO is often produced in a combined EO/EG process, which has the advantages that the EO process intrinsically has some glycols formation that requires work up, and that the combined process provides very efficient heat integration. The integrated process is usually split up into four sections: EO reaction and recovery; Light ends (LE) removal and EO purification; Glycols reaction and dewatering; and Glycols purification.

The present invention has application in the first section, EO reaction and recovery, which comprises an EO reactor in which EO is produced by catalytic gas phase oxidation of ethylene with a molecular oxygen-containing gas, a recycle loop for recycling unconverted reagents and removing products (EO, water and $CO_2$) and supplying fresh feeds, an EO Absorber and Stripper for EO recovery from absorbent by absorption in water and concentration, and a $CO_2$ removal section.

The general process conditions that apply for the EO recovery section in the prior art and also for the present invention are suitably an elevated temperature pressure. Herein an elevated temperature indicates a temperature above ambient. Similarly elevated pressure indicates a pressure in excess of atmospheric pressure. The recovery section may however operate at a temperature in the range of from ambient, for example 20° C., to 150° C., and a pressure in the range of from 100 to 1,000 kPa, for example from 200 to 400 kPa. An EO Stripper column will operate with a temperature and pressure differential from top to bottom.

Figure 1:
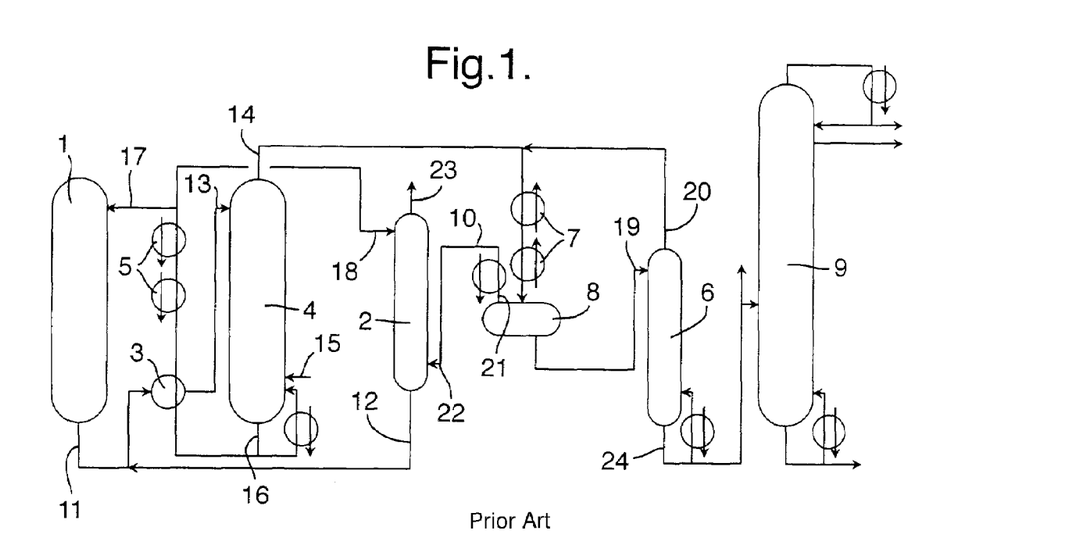
FIG. 1 illustrates a prior art EO/EG process and apparatus.

In a prior art system shown in FIG. 1, loopgas (not shown) from an EO Reactor enters the bottom part of the EO Absorber (1). The gas travels upwards and is washed with Lean Absorbent (LA) which is substantially EO-free. The almost EO-free top gas (not shown) is recycled back to the EO reactor system. In the EO absorber the EO is absorbed in the LA and exits as Fat Absorbent (FA) (11). FA (12) from the Residual Gas Absorber (RA) (2) is added to this stream. Cold FA (11, 12) flows through LA/FA heat exchanger (3) and is heated up.

The heated FA (13) enters the top of the EO Stripper (4). An EO/water mix leaves the EO Stripper over the top (14). In the bottom part of the EO Stripper heat is supplied by live steam or by means of a reboiler. Here also some LA is removed as glycol bleed and glycol removed from the LA. The water balance of the system is adjusted with a live steam or condensate stream (15) to the EO Stripper (4). Hot LA leaves the EO Stripper (4) over the bottom (16). In the LA/FA heat exchangers (3) the hot LA is cooled down. To get the correct temperature for absorption the LA is further cooled in other heat exchangers (5). The LA is then available for re-use in the EO Absorber (1) via line 17 and the RA (2) via line 18.

Analysis of the recovery section in one plant showed that in the EO Stripper approximately 30 MW of heat is used, whereas for the evaporation of EO only 7 MW is required. The explanation that much more heat is required in that plant is that about 17.5 MW is used to heat up LA and 7 MW is used to evaporate water out of the top of the EO Stripper. Moreover some impurities are present in the EO Stripper overhead which negatively affect the downstream EG process.

Accordingly there is a need to conserve energy which is currently consumed in evaporating a significant amount of water and removing it as vapour, and which appears to be unnecessary for separation purposes. Moreover there is a need to remove impurities originating in the EO process.

U.S. Pat. No. 4,875,909 (NSKK) discloses a method for the recovery of EO from such a process in order to reduce the heating energy of the EO Stripper. In this publication a prior art line up is disclosed in which a reduction of water in the EO Stripper overhead is achieved by creating a rectification in the EO Stripper with reflux of (partly) condensed top product. This refluxed material has to be evaporated again, costing energy. In this line-up, hot FA is fed to the upper part of an EO Stripper and (partly) condensed EO Stripper overhead vapor is returned to the top of the EO Stripper.

U.S. Pat. No. 4,875,909 discloses further line-ups to recover more heat from the top vapour of the EO Stripper and to recover heat from the EO Stripper bottoms using the following methods:

flash the bottom stream and apply vapour recompression of the flashed steam and use that steam in the EO Stripper use the bottom stream further as a heat medium in a refrigerator system use the bottom stream (after being used in other heat recovery possibilities) as a heat source in the EO Refiner located in the EO Stripper bottom stream, or in the LE Column.

In this publication the third characteristic of the apparatus and method relates to the heat content of the diffusate from the top of the EO Stripper. Lower heat content is achieved by lower water concentrations of the EO Stripper tops. This again is achieved by a reflux with partly condensed overhead vapors of the EO Stripper (in a reboiler of the LE Column). With less water going over the top, also less water has to be evaporated.

To make use of the heat content of the EO Stripper tops of this publication, even under conditions where it contains much less water, the pressure can be increased, in that way increasing the dew point. The heat content can then be used as a heat source for the EO Refiner.

SUMMARY OF THE INVENTION

We have now surprisingly found that by providing an additional FA feed, which is not heated, in the EO Stripper, an EO Stripper Concentrator stage is provided having particular heat duty advantages in terms of producing a concentrated top stream having reduced water content. Further advantageous embodiments have led to the further downstream advantage of combining the EO Stripper and the Residual Gas Absorber (RA) in a single unit.

Accordingly in a first aspect of the invention there is provided a process for the recovery of ethylene oxide (EO) from fat absorbent (FA) which comprises providing a feed of elevated temperature FA to an EO Stripper, providing a stripping gas feed and contacting the stripping gas fee at elevated temperature with the elevated temperature FA feed, obtaining stripped lean absorbent (LA) and an EO-containing gas, and providing one or more external process stream feeds to the EO Stripper at a location above the elevated temperature FA feed and at a lower temperature with respect to the elevated temperature FA feed thereby concentrating EO in the EO-containing gas.

The present invention also provides apparatus to perform the process of the invention which comprises an apparatus for recovery of ethylene oxide (EO) from fat absorbent (FA), which comprises an EO Stripper having an inlet for FA, an inlet for stripping gas, outlets for stripped lean absorbent (LA) and EO, and one or more inlets located above the FA inlet for one or more external process streams.

Accordingly there is provided an apparatus for recovery of EO from FA, comprising an EO Stripper having an inlet for elevated temperature FA, an inlet for stripping gas for contacting at elevated temperature with the elevated temperature FA, and outlets for stripped LA and EO, characterised in that the EO Stripper is an EO Stripper Concentrator for concentrating EO in the EO outlet, having one or more inlets located above the elevated temperature FA inlet for one or more external process streams at lower temperature with respect to the elevated temperature FA.

BRIEF DESCRIPTION OF THE DRAWINGS

FIGS. 2 to 11 illustrate the apparatus and process of the EO Stripper Concentrator of the invention.

DESCRIPTION OF PREFERRED EMBODIMENTS

Herein 'EO Stripper' and 'EO Stripper Concentrator' are used interchangeably when describing the adapted EO Stripper of the present invention.

In a particular advantage the one or more external process streams causes an increase in EO concentration and a decrease in water concentration in the overhead outlet of the EO Stripper Concentrator. The one or more external process streams condense water going up the EO Stripper Concentrator but the EO remains gaseous. This reduces reboiler duty.

A reflux by definition is carried out with introduction of (partly) condensed top product at the top of a column, the present invention therefore provides a Concentrator which differs from the prior art and from known refluxes by introducing an external process stream at the top of the EO Stripper Concentrator.

Reference herein to an external process stream is to a stream that is derived externally from a separate process unit in communication with the EO Stripper, and/or that is not a reflux stream, in particular is not a reflux stream from the EO Stripper or derived from the EO Stripper overhead, but more particularly is a concentrator stream for the EO Stripper tops internal. Preferably an external process stream is derived externally from a separate process unit directly without cooling, or indirectly but with only partial cooling. This has the particular advantage that the energy saving of the invention is not mitigated by energy used in cooling the concentrator stream.

Preferably the inlet for elevated temperature FA is located in the upper part of the EO Stripper and the inlet(s) for the one or more external process streams is located in the upper part of the EO Stripper above the inlet for introducing elevated temperature FA.

Accordingly in the present invention, for reduction of water content in the top, a rectifying section in the EO Stripper is not achieved with a reflux of top product, but is achieved using an external process stream as hereinbefore defined.

Preferably the apparatus is an apparatus for recovery of EO and comprises an EO Absorber which supplies the elevated temperature FA inlet of the EO Stripper Concentrator as hereinbefore defined, said EO Absorber having an inlet for an EO gaseous stream and an inlet for LA and an outlet for FA for heating and supply to the EO Stripper Concentrator. LA and FA are selected respectively from any aqueous absorbent for absorbing EO from a gaseous stream, or containing EO. Preferably LA and FA are respectively EO-lean and EO-fat aqueous absorbent. Absorbent is usually water optionally with any additives and entrained or accumulated process components.

Suitably stripping gas is any gas which is suitable for stripping EO from FA as hereinbefore defined, and is preferably selected from steam and the like.

Preferably elevated temperature FA supplied to an inlet is at a temperature in the range of from 60° C. to 150° C., preferably from 100° C. to 140° C. and the temperature of an external process stream supplied to an inlet as hereinbefore defined is in the range of from 10° C. to 80° C., preferably from 15° C. to 60° C. Preferably an external process stream is at a temperature in excess of the boiling point of EO.

Preferably the apparatus of the invention comprises inlets for supplying one or more external process streams to the EO Stripper in a ratio of 1 to 50 wt % external process stream expressed as a percentage of total external process streams, preferably with respect to elevated temperature FA, to 50 to 99 wt % elevated temperature FA, preferably in the range 5 wt % to 35 wt % external process streams to 65 wt % to 95 wt % elevated temperature FA.

An external process stream is suitably selected from an aqueous or gaseous stream, preferably an FA stream, a water stream, an EO stream and the like, and combinations thereof. An FA stream is suitably any available FA stream which is at a temperature lower than that of the elevated temperature FA. A water stream may be any available water stream, and may be make-up water balance or may be compensated elsewhere to restore the water balance in or related to the EO Stripper Concentrator.

An external process stream comprising water may make up part of the water balance in place of stripping gas, usually in the form of steam, or condensate which is normally added in the bottom of the EO Stripper. By adding water as external process stream as hereinbefore defined, in the top of the EO Stripper Concentrator, the same effect on the water balance may be achieved.

An external process stream comprising EO may comprise EO from elsewhere in the unit or from storage. Other external process streams may be envisaged using available feeds.

One or more external process stream inlets comprising FA inlets may be supplied from an outlet for FA from an EO Absorber for forming FA by contacting EO containing-gas and vapors with aqueous liquid phase LA, from an outlet for FA from an RA for forming FA by contacting residual EO-containing LE with aqueous liquid phase LA, or a combination thereof.

In the case that external process stream inlets comprising FA inlets are supplied from both sources, one or more combined inlets for external process stream FA may be supplied from the EO Absorber and the RA or one or more separate external process stream FA inlets may be supplied from the EO Absorber and the RA respectively.

The one or more external process streams comprising FA recovered from the EO Absorber usually passes via a LA/FA heat exchanger with hot LA on the other side supplied from an outlet in the bottom of the EO Stripper and supplying an inlet in the EO Absorber. The apparatus may comprise an RA in communication with the EO Absorber and EO Stripper Concentrator having an inlet for LA from the EO Stripper and an inlet for recovered light ends (LE) for conducting a further, residual, absorption of LE, and having outlets for FA and purified LE for recycle. Alternatively or additionally therefore, the one or more external process streams may comprise FA recovered from the RA which usually passes via a LA/FA heat exchanger with hot LA on the other side supplied from an outlet in the bottom of the EO Stripper and supplying an inlet in the RA.

The one or more external process stream inlets comprising FA inlets may be supplied from one of the RA or EO Absorber FA outlets, or a combination thereof, as a slip stream from the FA outlets, which bypasses or partially bypasses the LA/FA heat exchanger. The heat exchanger may accordingly be reduced, remain substantially the same size or may be increased in surface area.

In a particular advantage of the invention, an external FA stream must anyway be heated for stripping, and this is usually in the LA/FA heat exchanger. There is an energy saving by adding FA in the EO Stripper above the elevated temperature FA inlet, whereby the external process stream FA exchanges heat with the stripper contents, thereby concentrating the overhead.

In a further advantage by condensing part of the water in the top of the EO Stripper against FA, extra heat energy integration can be obtained that will be able to reduce the total steam consumption for an integrated EO/EG process.

In this case the apparatus and process of the invention provides for an energy gain due to condensing of the water in the top of the EO Stripper, thus heating up the cold FA which results in a lower energy requirement of the EO Stripper reboiler. A small energy loss in the EO Stripper due to less efficient recovery of energy in the LA/FA heat exchanger may be compensated by a small energy gain due to the higher temperature of the FA passing through the LA/FA heat exchanger, depending on the size of the heat exchanger.

In a particular advantage of the introduction of external process stream FA from the RA, the FA from the RA bottom is useful to absorb EO vapour in the EO Stripper top internal thereby reducing the total LA circulation. For example the RA circulates 20% FA and this can lead to a reduction of 5% total LA circulation. This further reduces energy consumption.

The RA may be supplied by a combined conduit for EO containing-LE from the Stripper and residual EO containing-LE from an overhead gas outlet from a LE Column which proceeds via in sequence a chiller, a cooler, a vent from a LE Surge Drum which condenses out EO and water and a further chiller; or may be supplied directly by residual EO containing-LE from the overhead gas outlet from the LE Column, bypassing the chiller, cooler, LE Surge Drum and further chiller; or a combination thereof. In the direct supply, the EO containing LE is supplied without condensing out EO and water. This represents a unit optimisation and may represent a change in overall energy consumption.

The apparatus of the invention may further comprise an inlet in the RA, suitably in the bottom part thereof, for external process stream FA. The external process stream FA is supplied from the EO Absorber, to absorb EO in the RA. FA still has some capacity to absorb EO from very EO-rich streams, whilst LA is required to absorb EO from EO-poor streams. Hence this adaptation represents a beneficial use of the absorbent available.

The apparatus of the invention may be operated at a desired pressure whereby variations in the above features may provide additional advantages. In particular, a chiller may be introduced for LE in the vent conduit from the LE Surge Drum to the RA inlet for residual EO-containing LE whereby pressure may be decreased or RA decreased in size, or vice versa.

In a further optimisation the RA is supplied directly by residual EO containing-LE from the overhead gas outlet from a LE Column, optionally via a condenser, and the surge drum and accumulator may be omitted in the overhead feed from the EO Stripper Concentrator to the LE Column.

In the apparatus of the invention, preferably in optimised form as hereinbefore defined, the RA may be located directly above the EO stripper as a separate unit or within a common shell forming a single column concentrator as a combined unit. Optionally additionally the LE Column may be incorporated within the combined EO Stripper and RA line up or shell, or it may be omitted.

Preferably the shell comprises an "overhead" between the EO Stripper portion and the RA portion to remove EO. This ensures that the EO does not all go into the RA. In this embodiment the EO overhead can go straight to the LE column, and LE overhead is fed to the RA.

Preferably an internal condenser, such as a cold water condenser, is provided in the top of the EO Stripper Concentrator which generates a reflux and further concentrates the overhead. In this case the LE Column may be omitted depending on the intended use of the product stream.

The RA may be decreased in size, due to the increase in EO concentration in the overhead and decrease in EO concentration in the LA.

In a further optimisation the RA may even be removed. In a particular advantage of the invention the improved line up has the consequence that by removing the RA there are no redundant streams and there is no need to divert streams. Again the LE Column may be omitted depending on the intended use of the product stream.

The RA and EO Stripper combined in a common shell may be in open communication or may comprise an internal division whereby each may be operated as a separate unit with independent operating conditions such as pressure and the like.

Combinations of the foregoing apparatus features and line ups may be envisaged by those skilled in the art.

In a further aspect of the invention there is provided a process for impurity removal in a process for the recovery of ethylene oxide (EO) from fat absorbent (FA) in an EO Stripper which comprises providing an elevated temperature FA feed, providing a stripping gas feed and contacting with the FA feed at elevated temperature in the EO Stripper, obtaining an overhead EO stream and a bottoms lean absorbent (LA) stream, and removing impurities through one or more side draws from the EO Stripper. The present invention also provides an apparatus for impurity removal in a process for recovery of EO from FA, comprising an EO stripper having an inlet for elevated temperature FA, an inlet for stripping gas for contacting at elevated temperature with the elevated temperature FA, an overhead outlet for EO and a bottoms outlet for LA, characterised in that the EO Stripper comprises one or more impurity removal stages in the form of one or more side draws from the EO Stripper intermediate the overhead and the bottom outlets for removing impurities.

Preferably the apparatus for impurity removal is an apparatus for recovery of EO from an EO-containing gas as hereinbefore described.

Suitably the apparatus removes hydrocarbon and chlorinated hydrocarbon impurities such as aldehydes, alcohols, acids, acetals, cyclic acetals, ethers, cyclic ethers, and esters, for example formaldehyde, 1,4-di-oxane, 1,4,7-tri-oxane, 1,3-di-oxolane, 2-methyl-1,3-di-oxolane, 2-chloro-methyl-1,3-di-oxolane, 2-chloro-ethanol, glyoxal, oxalic acid, glycolic acid, glyoxilic acid, lactic acid, acetic acid, formic acid, and their esters.

Preferably the side draw leads to a side stripper having a stripped gaseous phase outlet for purified gases, or leads to a converter for converting out EO and/or impurities, or to a bleed, or a combination thereof.

A side stripper or converter may comprise an outlet for a waste water stream or for an impurities-enriched stream.

A waste water stream or impurities-enriched stream may be separated from the side stripper as a bottom waste water stream or as a side impurities-enriched stream above a purified bottom water stream.

A side draw-off may be from any one or more locations in the EO Stripper and may be from the gas or liquid phase or a combination thereof; preferably it is from the liquid phase or combined gas and liquid phases. Preferably a side draw comprises a plurality of draw-off points at different levels or heights within the EO Stripper. This provides increased stability to fluctuations in EO concentration and impurity concentrations in the overhead and bottom and prevents build up of impurities. Moreover this provides for draw-off of different impurities.

Preferably an impurity-enriched stream is so concentrated in impurity that there is no waste water, and the enriched stream may therefore be discarded or reused within the system, for example as ballast or as part of the water balance.

Alternatively the side draw or impurity-enriched stream leads to a converter which converts EO or impurities to a product suitable for use or for discard, eg conversion of EO to MEG, esters to non-corrosive form, or the like.

Preferably the apparatus of the invention is for removing impurities which have a relative volatility between that of EO and water. In a particular advantage we have found that some impurities such as chlorinated cyclic acetals have a boiling point greater than both EO and water, for example of 200° C., whereby they might be expected to reside in a waste water stream, but that they have a relative volatility between that of EO and water, whereby they may surprisingly be separated from the bottom and top streams by the side draw of the invention.

Accordingly the apparatus for impurity removal is operated according to a single specification that the overhead comprises substantially no impurity, and that impurity builds up in the EO Stripper. Preferably the apparatus provides an overhead EO concentration of greater than or equal to 80 wt %, more preferably 88 wt %, more preferably 95 wt %, most preferably greater than or equal to 98 wt %, especialy greater than or equal to 99 wt % or 99.5 wt %. Thereby the overhead is substantially free of some or most impurities.

Preferably the apparatus for impurity removal comprises means for concentrating the overhead from the EO Stripper. Thereby in a particular advantage substantially all impurities are concentrated within the EO Stripper and do not leave via the overhead, whereby substantially pure overhead is obtained. The EO Stripper may comprise a reflux in the top of the EO Stripper or in the overhead. This concentrates the overhead, for example gives approximately 80 wt % EO or more preferably 88 wt % EO in the overhead.

Alternatively or additionally an apparatus for impurity removal is present in an EO Stripper Concentrator of the first aspect of the invention comprising means for concentrating the overhead as hereinbefore described. In a particular advantage in the apparatus comprising a liquid side draw any residual impurities above the side draw are condensed within the EO Stripper Concentrator as hereinbefore defined by means of the external process stream inlets as hereinbefore defined. Thereby the overhead is further concentrated, and for example comprises approximately 90 wt % EO. More preferably the apparatus for impurity removal is present in an EO Stripper Concentrator comprising additionally a reflux in the top of the EO Stripper Concentrator or in the overhead. Thereby the overhead is further concentrated, and for example comprises approximately 99 wt % or more EO. We have found that this impurity removal has excellent effect due to highly concentrated overhead.

In a particular advantage of the further embodiment of the invention comprising a side stripper to the EO Stripper, the removal of impurities reduces downstream problems such as corrosion, product quality, waste generation and the like.

Preferably an apparatus of the present invention is part of an EO/EG unit for the conversion of ethylene to EO, and thereafter to EG, or purified to high purity EO, comprising an EO Absorber having an inlet for reaction gas and an inlet for Absorbent, and an outlet for FA comprising EO, and comprising an EO Stripper having an inlet for elevated temperature FA and outlets for stripped LA and for EO, the apparatus comprising additionally one or more inlets in an EO Stripper Concentrator for external process streams for concentrating the EO outlet stream, and/or comprising one or more impurity removal stages in the form of one or more side draws from the EO Stripper or EO Stripper Concentrator as hereinbefore defined.

As hereinbefore described in one aspect of the invention there is provided a process for recovery of EO from FA comprising providing a feed of elevated temperature FA to an EO Stripper, providing a stripping gas feed and contacting at elevated temperature with the elevated temperature FA feed, and obtaining stripped LA and an EO containing gas, characterised by providing one or more external process stream feeds to the EO Stripper at a location above the elevated temperature FA feed thereby providing an EO Stripper Concentrator for concentrating EO in the EO containing gas, and at a lower temperature with respect to the elevated temperature FA feed.

The process of the invention gives a purified EO product stream from the overhead of the EO Stripper Concentrator which is more concentrated in EO and less concentrated in water vapour and impurities than the corresponding process without external process stream feed. The one or more external process stream feeds condense water going up the EO Stripper but the EO remains gaseous.

Preferably the water content in the EO stripper overhead stream in the process of the invention is in the range from pure EO to 30 wt % water. Preferably the process provides an EO Stripper overhead stream comprising higher EO concentration, in comparison to the prior art process. This leads to savings on stripper duty and low pressure steam savings.

The present invention is a novel way to reduce the water content in the EO Stripper tops, by for example using FA feed partially bypassing the FA feed bottoms exchanger or by using external process stream feeds as hereinbefore defined from elsewhere. By having an external process stream feed at a lower temperature than the FA feed, in the top of the Stripper the water in the top is condensed with the external process stream FA stream, thus reducing the duty of the reboiler and providing a more energy efficient process. Other process modifications also become possible leading to a simpler operation and lower energy demands.

The process of the invention is characterised by further advantages corresponding to those as hereinbefore stated for the hereinbefore defined apparatus.

Preferably the process comprises providing the feed of elevated temperature FA in a stripped vapors zone in the upper part of the EO Stripper Concentrator, and providing the one or more feeds of one or more external process streams in the upper part of the EO Stripper Concentrator, above the feed for elevated temperature FA.

Preferably the process is a process for recovery of EO and comprises absorbing EO with LA and obtaining FA for heating to elevated temperature and supply of elevated temperature FA feed to the EO Stripper Concentrator as hereinbefore defined.

Preferably an elevated temperature FA feed as hereinbefore defined is at a temperature in the range of from 60° C. to 150° C., preferably from 100° C. to 140° C., and the temperature of an external process stream is in the range of from 10° C. to 80° C., preferably from 15° C. to 60° C. Preferably the external process stream is at a temperature in excess of the boiling point of EO.

The process may comprise providing one or more external process stream feeds to the EO Stripper in a ratio of 1 to 50 wt % external process stream expressed as a percentage of total external process streams, preferably with respect to elevated temperature FA, to 50 to 99 wt % elevated temperature FA, preferably in the range 5 wt % to 35 wt % external process streams to 65 wt % to 95 wt % elevated temperature FA. Whilst there is no limitation as such on the amount of external process stream FA to introduce, and the input to the EO Stripper might comprise up to 100% external process stream FA, without the need to introduce additional steam, particularly significant concentration effect is obtained with external process streams in proportions as hereinbefore described.

Preferred external process stream feeds are as hereinbefore described. By selecting the nature of external process stream feed, the concentration of EO in the EO Stripper overhead may be influenced to advantage.

The one or more external process stream feeds comprising FA may comprise FA from an EO Absorber for forming FA by contacting EO containing-gas and vapors with aqueous liquid phase LA, or may comprise FA from an PA for forming FA by contacting residual EO-containing LE with LA, or a combination thereof.

In the case that external process stream feeds comprise FA from both sources, one or more combined feeds for external process stream FA feed may be supplied from the EO Absorber and the RA or one or more separate external process stream FA feeds may be supplied from the EO Absorber and the RA respectively.

The one or more external process stream feeds comprising FA feed from the EO Absorber usually passes via a LA/FA heat exchanger with hot LA on the other side supplied from the bottom of the EO Stripper as feed to the EO Absorber. The process may comprise providing an LA feed from the EO Stripper to a RA, in communication with the EO Absorber and EO Stripper Concentrator, and contacting with a recovered LE feed for conducting a further, residual, absorption of LE, and obtaining FA and purified LE for recycle. Alternatively or additionally therefore, the one or more external process stream feeds may comprise FA recovered from the RA which usually passes via a LA/FA heat exchanger with hot LA on the other side obtained from the bottom of the EO Stripper as feed for the RA.

The one or more external process stream feeds comprising FA may be obtained from one of the RA or EO Absorber, or a combination thereof, as a slip stream from the FA streams, which bypasses or partially bypasses the LA/FA heat exchanger. The heat exchange duty may accordingly be reduced, remain substantially the same or may be increased.

The process may comprise supplying the RA from a combined EO containing-LE feed from the Stripper and residual EO containing-LE feed from the overhead from a LE Column via in sequence a chiller stage, a cooler stage, venting from a LE Surge Drum which condenses out EO and water and a further chiller stage; or supplying directly residual EO containing-LE feed from the overhead from the LE Column, bypassing the chiller stage, cooler stage, condensation and further chiller stage; or a combination thereof. In the direct supply process, EO containing-LE feed is supplied without condensing out EO and water. This represents a process optimisation and may represent a change in overall energy consumption.

The process may further comprise supplying external process stream FA in the RA, preferably in the bottom part thereof. The external process stream FA is supplied from the EO Absorber to absorb EO in the RA.

The process of the invention may be operated at a desired pressure, preferably from above atmospheric pressure up to 4 bar (400 kpa), whereby variations in the above features may provide additional advantages. In particular, a chilling stage may be introduced for residual EO-containing LE vented from the LE Surge Drum and supplying to the RA whereby pressure may be decreased or RA volumes decreased, or vice versa.

In a further embodiment the process comprises supplying the RA directly with residual EO containing-LE from the overhead from a LE Column, optionally via a condenser stage and omitting a surge and accumulator stage in the overhead feed from the EO Stripper Concentrator to the LE Column.

In the process of the invention, preferably optimised as hereinbefore described, the RA stage may be conducted directly above the EO Stripper Concentrator stage in separate process stages or within a common shell forming a single column concentrator as a combined process stage. Optionally additionally a LE separation stage may be incorporated within the EO Stripper and RA stages or integral therewith.

Preferably the shell comprises an "overhead" between the EO Stripper portion and the RA portion to remove EO. This ensures that the EO does not all go into the RA. In this embodiment the EO overhead can go directly as feed to the LE column, and LE overhead is feed to the RA.

Preferably a reflux, such as a cold water reflux, for example generated by an internal condenser, is provided in the top of the EO Stripper Concentrator which further concentrates the overhead. In this case the separation stage in the LE Column may be omitted depending on the intended use of the product stream.

The RA stage may be decreased in size, due to the increase in EO concentration in the overhead and decrease in EO concentration in the LA.

In a further optimisation the RA stage may even be removed. Again the separation stage in the LE Column may be omitted depending on the intended use of the product stream.

The RA and EO Stripper combined in a common shell may be integral or may be operated as separate processes with independent operating conditions such as pressure and the like.

Combinations of the foregoing process features may be envisaged by those skilled in the art.

As hereinbefore described in a further aspect of the invention there is provided a process for impurity removal in a process for recovery of EO from FA in an EO Stripper comprising an elevated temperature FA feed for contacting with stripping gas at elevated temperature, and obtaining an overhead EO stream and a bottoms LA stream, characterised in that the EO Stripper comprises one or more impurity removal stages in the form of one or more side draws from the EO Stripper for removing impurities intermediate the overhead and bottoms streams.

Preferably the process for impurity removal is a process for recovery of EO from an EO-containing gas.

Suitably the process removes hydrocarbon and chlorinated hydrocarbon impurities such as aldehydes, alcohols, acids, acetals, cyclic acetals, ethers, cyclic ethers, and esters, for example formaldehyde, 1,4-di-oxane, 1,4,7-tri-oxane, 1,3-di-oxolane, 2-methyl-1,3-di-oxolane, 2-chloro-methyl-1,3-di-oxolane, 2-chloro-ethanol, glyoxal, oxalic acid, glycolic acid, glyoxilic acid, lactic acid, acetic acid, formic acid and their esters.

Preferably the side draw feeds a side stripper having a stripped gaseous phase outlet for purified gases, or feeds a converter for converting EO and/or impurities, or feeds a bleed, or a combination thereof.

A side stripper or converter stage may produce a waste water stream or an impurities-enriched stream. A waste water stream or impurities-enriched stream may be separated from the side stripper as a bottom waste water stream or as a side impurities-enriched stream above a purified bottom water stream.

A side draw off may be from any one or more locations in the EO Stripper and may be from the gas or liquid phase or a combination thereof, preferably is from the liquid phase or combined gas and liquid phases. Preferably a side draw comprises a plurality of draw off points at different levels or heights within the EO Stripper. This provides increased stability to fluctuations in EO concentration and impurity concentrations in the overhead and bottom and prevents build up of impurities. Moreover this provides for draw off of different impurities.

Preferably an impurity-enriched stream is so concentrated in impurity that there is no waste water, and the process comprises discarding the enriched stream or reusing within the system, for example as ballast or as part of the water balance.

Alternatively the process comprises providing the side draw or impurity-enriched stream to a converter and converting EO or impurities to a product suitable for use or for discard, eg conversion of EO to MEG, esters to non-corrosive form, or the like.

Preferably the process of the invention is for removing impurities which have a relative volatility between that of EO and water. In a particular advantage we have found that some impurities such as chlorinated cyclic acetals have a boiling point greater than both EO and water, for example of 200° C., whereby they might be expected to reside in a waste water stream, but that they have a relative volatility between that of EO and water, whereby they may surprisingly be separated from the bottom and top streams by the side draw of the invention.

Accordingly the process is operated according to a single specification that the overhead comprises substantially no impurity, and that impurity builds up in the EO Stripper. Preferably the process provides an overhead EO concentration of greater than or equal to 80 wt %, more preferably 88 wt %, more preferably 95 wt %, most preferably greater than or equal to 98 wt %, and especially preferably greater than or equal to 99 wt % or 99.5 wt %. Thereby the overhead is substantially free of some or most impurities.

Preferably the process comprises providing a side draw-off in the gaseous and/or liquid phase of the EO Stripper, preferably at the point of greatest concentration of impurities, typically the upper to middle distillation stages in the EO Stripper such as the third, fourth or fifth concentrator tray in say a 20 stage EO Stripper column. Any impurities leaving the EO Stripper via the bottom will lead to accumulation of impurities in the LA/FA circuit which are then drawn off in the side draw of the EO Stripper.

Preferably the process comprises concentrating the overhead from the EO Stripper. Thereby in a particular advantage substantially all impurities are concentrated within the EO Stripper and do not leave via the overhead, whereby substantially pure overhead is obtained. The process may comprise operating a reflux in the top of the EO Stripper or in the overhead. This concentrates the overhead, for example gives approximately 80 wt % or more preferably 88 wt % EO in the overhead.

Alternatively or additionally a process for impurity removal is present in a EO Stripper Concentrator process of the first aspect of the invention comprising means for concentrating the overhead as hereinbefore described. In a particular advantage in the process comprising providing a liquid side draw any residual impurities above the side draw are condensed within the EO Stripper Condensor as hereinbefore defined by means of the external process stream inlets as hereinbefore defined. Thereby the overhead is further concentrated, for example comprises approx 90 wt % EO. More preferably the process for impurity removal is present in an EO Stripper Concentrator process as hereinbefore defined comprising additionally a reflux in the top of the EO Stripper Concentrator on in the overhead. Thereby the overhead is further concentrated, for example comprises approx 99 wt % or more EO. We have found that this impurity removal has excellent effect due to highly concentrated overhead.

In a further advantage the external process stream concentrator process of the invention causes condensation of heavy contaminants above the flasher of the EO Stripper and avoids contaminants leaving in the EO Stripper overhead. In particular this is useful for heavy contaminants such as chlorinated hydrocarbons, including alcohols, organic acids, aldehydes, acetals and esters.

Preferably a process of the invention is part of an EO/EG process for the conversion of ethylene to EO with formation of byproducts, water and $CO_2$, and thereafter converting to EG, or purifying to high purity EO, comprising recovering EO by introducing into an EO absorber and contacting with absorbent to form FA and introducing elevated temperature FA into an EO stripper to separate absorbent from product EO, the process comprising additionally introducing one or more external process stream feeds into the EO Stripper Concentrator by the process as hereinbefore described and/or comprising one or more impurity removal stages in the form of one or more side draws to the EO Stripper or EO Stripper Concentrator as hereinbefore defined.

The invention is now illustrated in non-limiting manner with respect to the following Examples and Figures.

In FIG. 1 the overhead product (14) of the EO Stripper (4) is partly condensed against chiller and/or coolers (7) and sent via line (19) to the LE Column (6) for removal of light components. The overhead vapour (20) of the LE Column is sent back to the LE Column Surge Drum (8). The light components gas stream is vented from the LE Column Surge Drum, passes through the RA (2) via line 22 to recover EO and is sent back to the recycle gas (23) by means of the Residual Gas Compressor (not shown).

The RA (2) is operated with cold LA (18) as scrubbing medium and the bottom stream (12) is combined with the FA (11) from the EO Absorber (1) and sent back to the EO Stripper (4) via line 13 for recovery of the EO.

The bottom stream (24) of the LE Column (6), essentially a water/EO mixture, is fed either to an EO Purification Column (9) for recovery of high purity EO and/or fed directly to a Glycol Reactor (not shown).

In the prior art process of FIG. 1 if the pressure in the EO Stripper (4) is lowered, an optional chiller (10) may be present in the LE gas stream (21) from the LE column Surge Drum (8).

Figure 2:
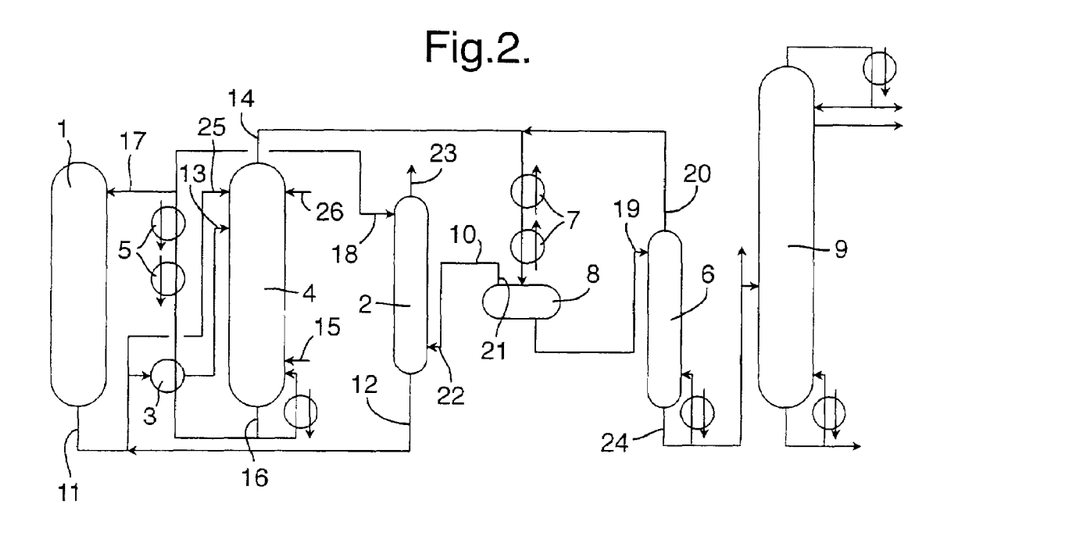

In FIG. 2 the FA (11) from the bottom of the EO Absorber (1) is combined with the bottom stream (12) of the RA (2) as in FIG. 1, and part of this mixture is introduced as external process stream feed (25) to the EO Stripper Concentrator (4), above the elevated temperature FA feed (13) and at a lower temperature thereto.

Alternatively or additionally optional external process stream feed(s) (26) to the EO Stripper Concentrator (4) is/are from another external source. Such external process stream (26) may optionally also be present in the apparatus and method illustrated in the subsequent FIGS. 3 to 11 (there not shown).

Figure 3:
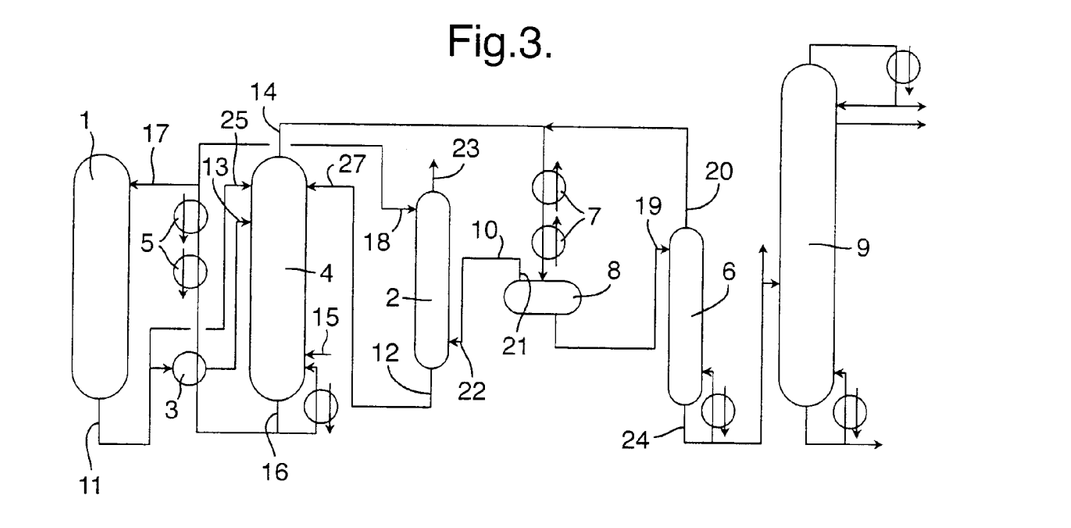

In FIG. 3 there is no combination of FA from the bottom (11) of the EO Absorber (1) with the bottom stream (12) of the RA (2) as in FIG. 2, rather they are fed separately (25, 27) to the EO Stripper. Part of the cold FA (11) from the EO Absorber and the bottom stream (12) of the RA (2) are used as external process stream feed (25, 27) to the EO Stripper Concentrator (4) to get the same effect as in FIG. 2.

Figure 4:
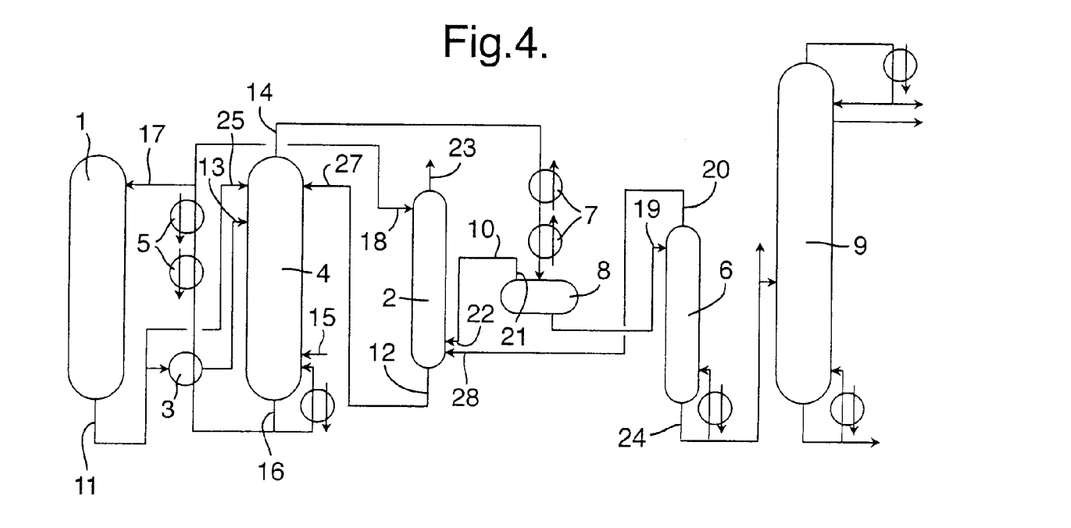

In FIG. 4 the overhead gas (20) from the LE Column (6) is no longer condensed against cooling water and a chiller as in FIGS. 1 to 3, but instead is absorbed (28) in the RA (2).

Figure 5:
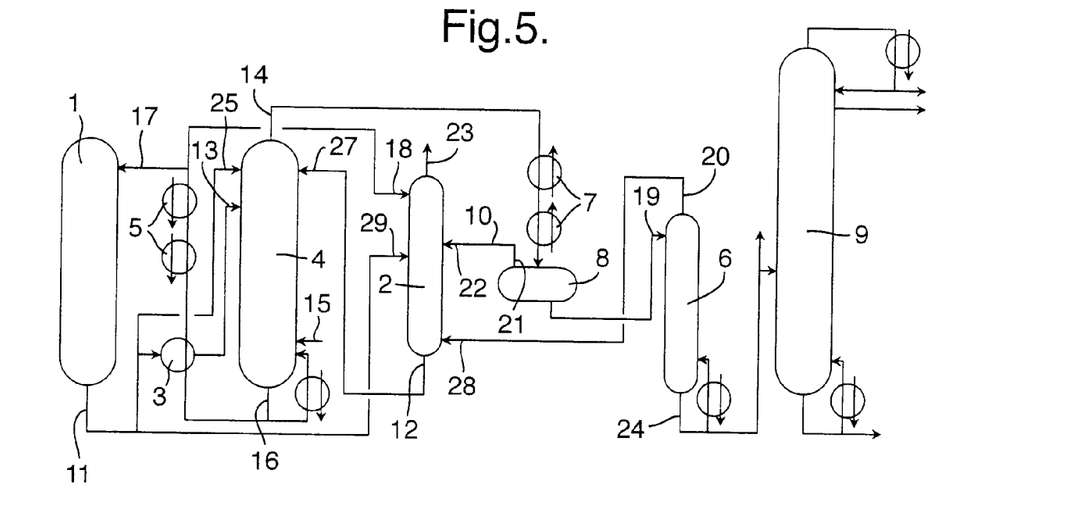

In FIG. 5 the RA (2) line up is optimised: a small portion of the cold FA stream (11) of FIGS. 1 to 4 is used (29) to absorb EO in the bottom part of the RA (2), whereas LA (18) is used in the top part.

Figure 6:
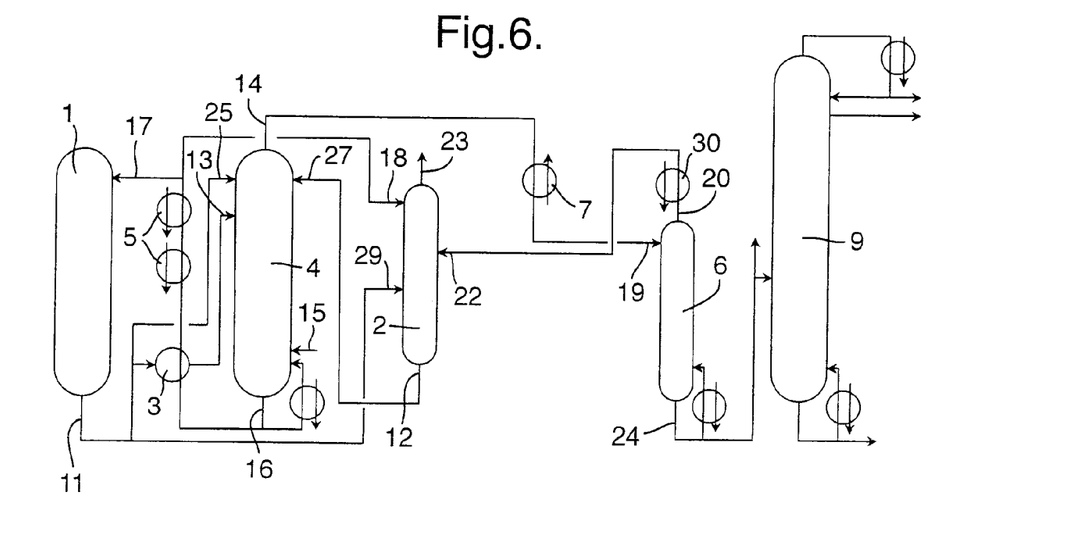

FIG. 6 shows the system of FIG. 4 wherein the function of the accumulator between the EO Stripper condensers (7) and the LE Column (6) in the original outlet is redundant, and these units can be removed. An optional chiller (30) may be included in the overhead (20) from the LE Column (6) to the inlet (22) to the RA (2).

Figure 7:
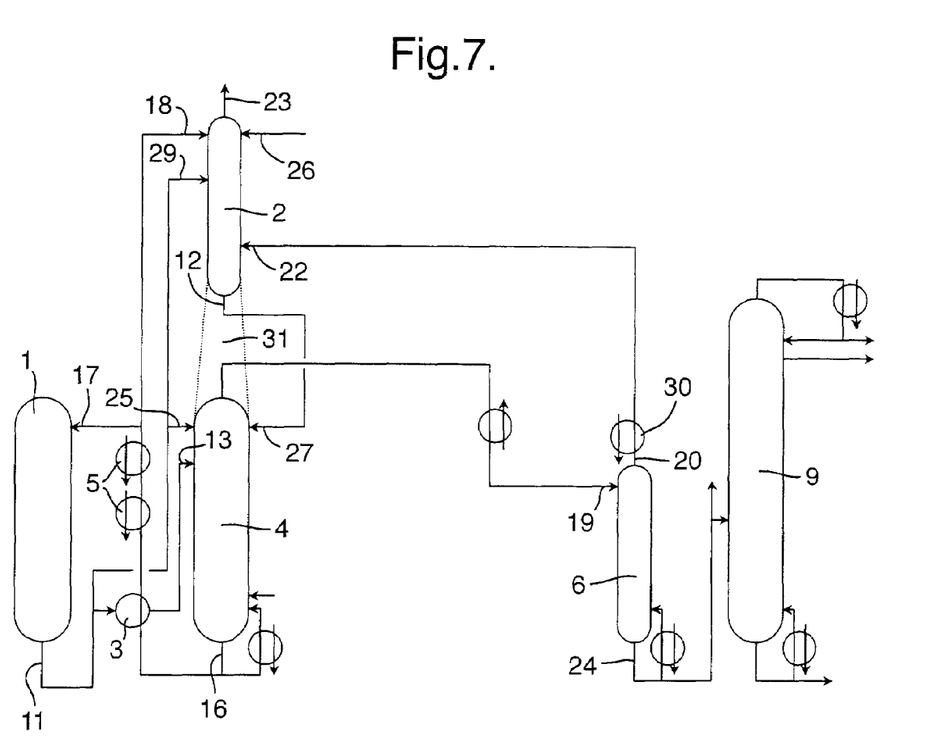
Figure 8:
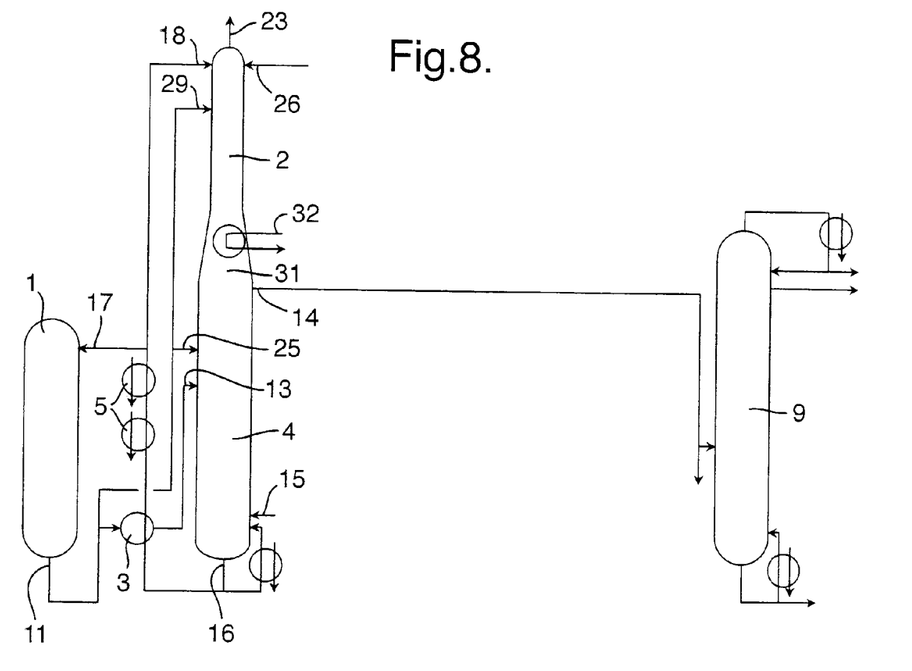

FIGS. 7 and 8 show the same functional system of FIG. 6 but with the RA (2) located on top of the EO Stripper (4) or integrated with the EO Stripper (4) into one shell (31). The integrated single shell (31) may have different or same diameters. In the combined shell configuration (31) shown in FIG. 8 the LE Column may be omitted.

FIG. 8 shows the system of FIGS. 2 to 9 with integrated shell (31) and means for condensing the EO Stripper overhead by reflux (32) to give an overhead stream (14) of greater than or equal to 99 wt % EO. This line up provides for very high concentration EO in the EO Stripper overhead such that the overhead can go direct to EO purification and the LE Column is dispensed with. The residual LE, eg $CO_2$, is acceptable in feedstock to downstream processes such as an EG process. If LE removal is desired a stripper in the overhead (not shown) may be included.

Figure 9:
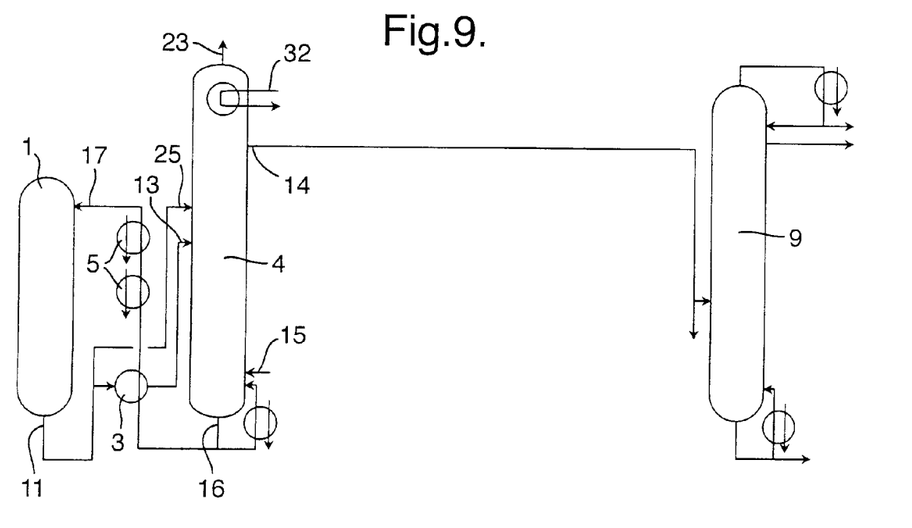

FIG. 9 shows the system of FIG. 8 with the RA completely removed. An LE column may be present if desired depending on the intended use of the product stream (14).

Figure 10:
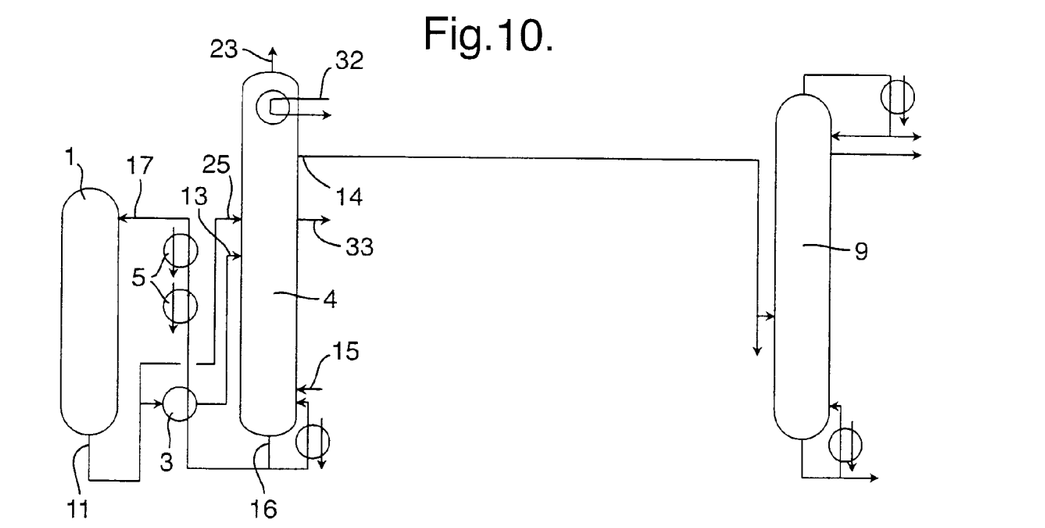
FIGS. 10 to 11 illustrate the apparatus and process of the EO Stripper impurity removal of the invention.

FIG. 10 shows the side draw (33) for impurity removal with means for condensing in the form of an overhead reflux (32) of FIGS. 8 and 9 and optionally additionally with the external process stream concentrator (25, 27) of FIGS. 2 to 8.

Figure 11:
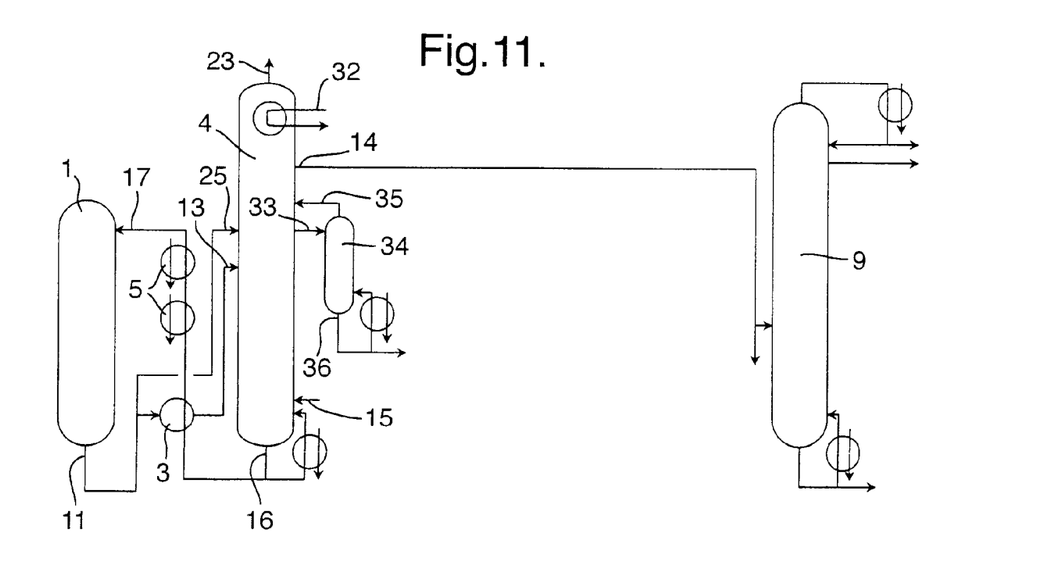

FIG. 11 shows the system of FIG. 10 leading to a side stripper (34) with return of purified EO (35) to the EO Stripper (4), and removal of impurities in a waste water stream or a concentrated impurity stream (36). In this line up, for example, the EO Stripper (4) may comprise 20 theoretical stages, with the elevated temperature FA feed (13) entering the column preferably at stages 6 to 9, e.g. stage 9, any lower temperature FA feed (25) entering above preferably at stages 5 to 7, e.g. stage 6, and with the side draw-off preferably at stages 3 to 5, e.g. at stage 4, to the side stripper (34) having some 5 theoretical stages. As an alternative to theoretical stages, or plates provided by packing, one or both stripper columns may operate with physical trays.

EXAMPLE 1

In the system of FIG. 2 with 20% bypass of FA we get 5.8% $H_2O$ in EO stripper overhead.

| | |
|---|---|
| Energy necessary to evaporate EO | 4941 kW |
| Energy necessary to heat up FA in column | 30159 kW |
| Energy necessary to evaporate water | 11293 kW |

For bypass of 0%-20% cold FA the following results are obtained:

TABLE 1

| | % bypass | | | | |
|---|---|---|---|---|---|
| | 0 | 5 | 10 | 15 | 20 |
| Reduction water over top [kW] | 0 | −4054 | −8108 | −12162 | −16216 |
| Energy loss due to bypass in LA/FA heat | 0 | 4369 | 8739 | 13108 | 17477 |

TABLE 1-continued

| | % bypass | | | | |
|---|---|---|---|---|---|
| | 0 | 5 | 10 | 15 | 20 |
| exchanger (3) [kW] | | | | | |
| Energy gain due to higher hot FA temperature [kW] | 0 | −1780 | −3379 | −4779 | −5997 |
| Reduction of energy content EO Concentrator tops [kW] | 0 | −296 | −591 | −887 | −1183 |
| Overall duty reduction [kW] | 0 | −1761 | −3334 | −4720 | −5919 |

Optimum bypass is estimated at 25%-30% giving a heating duty reduction of approx 10 MW.

EXAMPLE 2

For the apparatus and methods of FIGS. 1 and 11, Table 2 shows impurity levels in the EO Stripper/Concentrator top, and the associated energy performance.

| | FIG. 1 | FIG. 11 |
|---|---|---|
| Heat duty EO Stripper/Concentrator/Mwatt | 64.5 | 58.5 |
| Duty side stripper (34)/Mwatt | | 0.5 |
| Feed temperature FA1 (13)/° C. | 104.5 | 111.2 |
| Feed temperature FA2 (25)/° C. | | 37 |
| FA1 t/h (13) | 1911.2 | 1624.5 |
| FA2 t/h (25) | | 286.7 |
| Temp EO Stripper/Concentrator Top (14)/° C. | 99.7 | 26.0 |
| Temp EO Stripper/Concentrator Bottom (16)/° C. | 119.4 | 120.9 |
| EO purity OVHD EO Stripper/Concentrator (14)/% | 64.50 | 99.60 |
| Impurity top EO Stripper/Concentrator (14)/ppm | 17.0 | 0.89 |

From the Table it is clear that impurity removal may be operated with the FA bypass of Example 1 and still gain an energy reduction compared to the conventional operation with no impurity removal. Impurity removal results in a reduction from 17 ppm to 0.89 ppm impurity in the EO Stripper/Concentrator top.

What is claimed is:

1. A process for the recovery of ethylene oxide (EO) from fat absorbent (FA), said process comprising:
   providing a feed of elevated temperature FA to an EO Stripper,
   providing a stripping gas feed and contacting the stripping gas feed at elevated temperature with the elevated temperature FA feed,
   obtaining stripped lean absorbent (LA) and an EO-containing gas, and
   providing one or more external process stream feeds to the EO Stripper at a location above the elevated temperature FA feed and at a lower temperature with respect to the elevated temperature FA feed thereby concentrating EO in the EO-containing gas.

2. The process of claim 1, wherein said FA feed is at a temperature in the range from 60° C. to 150° C. and the external process stream feed temperature is in the range of from 10° C. to 80° C.

3. The process of claim 1, wherein the total of the one or more external process stream feeds to the EO Stripper comprise 1 to 50 wt % of the combined external process stream feeds and elevated temperature FA.

4. The process of claim 1, wherein an external process stream feed is derived externally from a separate process unit directly without cooling, or indirectly but with only partial cooling.

5. The process of claim 1, wherein an external process stream feed is selected from the group consisting of a FA stream; a water stream; an EO stream; and combinations thereof.

6. The process of claim 1, wherein an external process stream feed comprises FA from an EO Absorber for forming FA by contacting EO containing-gas and vapors with aqueous liquid phase LA.

7. The process of claim 1, wherein an external process stream feed comprises FA from a residual gas absorber (RA) for forming FA by contacting residual EO-containing light ends (LE) with LA.

8. The process of claim 7, wherein the external process stream feed further comprises FA from an EO Absorber for forming FA by contacting EO containing-gas and vapors with aqueous liquid phase LA.

9. The process of claim 1, wherein a first external process stream feed comprises FA from an EO Absorber for forming FA by contacting EO containing-gas and vapors with aqueous liquid phase LA and a second external process stream feed comprises FA from a residual gas absorber (RA) for forming FA by contacting residual EO-containing light ends (LE) with LA.

10. The process of claim 7, wherein the residual gas absorber (RA) is conducted directly above the EO Stripper as a separate process stage.

11. The process of claim 7, wherein the residual gas absorber (RA) is conducted within a common shell with the EO Stripper forming a single column concentrator as a combined process stage.

12. The process of claim 1, wherein a reflux generated by an internal condenser is provided in the top of the EO Stripper.

* * * * *